United States Patent [19]

Siegmann et al.

[11] Patent Number: 4,564,021
[45] Date of Patent: Jan. 14, 1986

[54] MOUTHPIECE FOR A BREATH-ALCOHOL MEASURING DEVICE

[75] Inventors: Klaus Siegmann, Lubeck; Martin Schmidt, Bad Schwartau, both of Fed. Rep. of Germany

[73] Assignee: Dragerwerk AG, Fed. Rep. of Germany

[21] Appl. No.: 692,726

[22] Filed: Jan. 18, 1985

Related U.S. Application Data

[63] Continuation of Ser. No. 522,662, Aug. 12, 1983, abandoned.

[30] Foreign Application Priority Data

Sep. 9, 1982 [DE] Fed. Rep. of Germany ....... 3233462

[51] Int. Cl.$^4$ ...................... A61M 16/00; A61B 10/00
[52] U.S. Cl. ................................. 128/716; 128/207.14
[58] Field of Search .................. 128/716, 730, 201.26, 128/206.29, 207.14, 207.15

[56] References Cited

U.S. PATENT DOCUMENTS

| | | | |
|---|---|---|---|
| 471,389 | 3/1892 | Lacy | 728/727 |
| 3,880,591 | 4/1975 | Burroughs | 128/716 |
| 4,259,951 | 4/1981 | Chernak et al. | 128/725 X |
| 4,263,921 | 4/1981 | Frugillo | 128/201.14 X |
| 4,292,978 | 10/1981 | Guth | 128/730 |
| 4,360,017 | 11/1982 | Barlett | 128/207.14 |

FOREIGN PATENT DOCUMENTS 2820916 11/1980 Fed. Rep. of Germany.

Primary Examiner—Edward M. Coven
Attorney, Agent, or Firm—McGlew and Tuttle

[57] ABSTRACT

A tested person blows into an alcohol-breath measuring device through the mouthpiece. The mouthpiece must be kept under hygienic conditions and must be disposable, thus designed for single use by a tested person. The mouthpiece is an integral part injection molded of polypropylene, having a mouth portion, and a portion connecting to the measuring device and extending through the bottom of the mouth portion into the interior thereof. The tested person takes the mouthpiece between his lips and exhales through the connecting portion into the device. A limiting flange on the outside of the mouth portion limits the penetration thereof in the mouth and keeps saliva from the surface intended for holding. The mouthpiece may accommodate a check valve. A valve insert received in the mouth portion holds a valve plate which under the blow, elastically disengages from apertures in the bottom of the insert and applies against these apertures again as soon as the blowing ceases or the tested person inhales.

3 Claims, 2 Drawing Figures

MOUTHPIECE FOR A BREATH-ALCOHOL MEASURING DEVICE

This is a continuation, of application Ser. No. 522,662 filed Aug. 12, 1983, abandoned.

FIELD AND BACKGROUND OF THE INVENTION

This invention relates in general to gas detection devices and in particular to a new and useful mouthpiece construction for a breath alcohol measuring device.

All over the world, there are commercially available breath-alcohol measuring devices into which breath is to be blown by a person being tested. For this purpose, such devices are equipped with a mouthpiece which must comply with certain requirements. They must be hygienically handled, and preferably exchangeable after use, thus disposable. Consequently, they must be inexpensive in manufacture.

A prior art mouthpiece for breath testing apparatus comprises a set of two members, namely a cup and a connection piece. The connection piece is passed through the bottom of the cup. In the interior of the cup, the connection piece terminates by a closed end and radial apertures. The complete mouthpiece is to be connected to the breath measuring device by the outer end of the connection piece. During the breath test, the mouthpiece is pressed around the mouth against the face so that the rim of the cup sealingly surrounds the lips. The connection piece end protruding inside prevents saliva particles from being entrained. Foreign particles are rather separated by deflection, and they are collected in the lower part of the cup (U.S. Pat. No. 3,880,591). The mouthpiece, however, has no stop for inhalation or suction, so that an awkward blowing may both disturb the function of the measuring device and infect the tested person with germs which might escape therefrom.

Another prior art mouthpiece for the measuring head of a device for detecting alcohol in the breath is tubular and accommodates a check valve closing in the direction of inhalation. The mouthpiece is exchangeable. At one of its ends, the tubular mouthpiece is closed with a bottom. The breath outlet is provided below the check valve, in the side wall of the tube and at a location spaced from the bottom, so that a saliva collecting chamber is formed between the bottom and the outlet (German Pat. No. 28 20 916). The breath air leaves the mouthpiece laterally, wherefore no application is possible to conventional breath-alcohol measuring devices. Complicated tools are required for the manufacture which is therefore expensive.

SUMMARY OF THE INVENTION

The present invention is directed to a mouthpiece which, in order to satisfy the high hygienic requirements, is intended for a single use, and must therefore be simple and inexpensive in manufacture.

In accordance with the invention, a mouthpiece for a breath alcohol measuring device comprises a hollow cylindrical mouth-portion having an open tubular mouth engaging end and an opposite closed end. The hollow tubular connecting portion has an open exterior end and an opposite interior closed end which extends through the closed end of the mouth portion and into the interior thereof. The interior closed end includes a portion adjacent the end with a lateral breath inlet. The mouth portion has a diameter and a wall thickness suitable for taking a mouthpiece into a person's mouth and it includes a flange portion projecting from the exterior thereof at a spaced location from its open end limiting the length of penetration of the mouthpiece into the person's mouth.

The invention has the advantage that instead of a cup which is to be applied around the mouth to firmly hold the mouthpiece in place, and certainly poses additional problems with bearded persons, a firm mouthpiece can be held in the mouth. No further handling is needed. The circumferential limiting flange insures the right introduction into the mouth and, in addition, prevents saliva from flowing out.

The inventive mouthpiece is advantageously equipped with a check valve. The additional parts are simple and reliable in operation and may be injection-molded. The disposability of the inventive mouthpiece is justified by the possibility of manufacturing it in a simple and inexpensive way as a single injection-molded piece. The same goes for the parts forming the valve which may easily be inserted into conventional mouthpieces too.

Accordingly, it is an object of the invention to provide an improved disposable mouthpiece for a breath analyzing device which includes a mouthpiece portion having an exterior limiting flange and a connecting portion of the diameter of the parts to which it is to be connected which terminates inside the mouthpiece portion in a closed end with a lateral opening adjacent the closed end for the inflow of the drawn in air.

A further object of the invention is to provide a mouthpiece construction which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
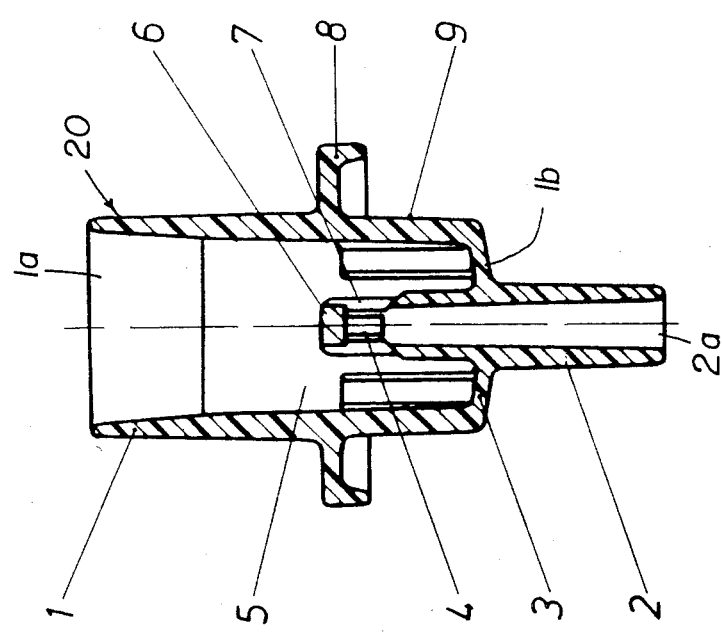
FIG. 1 is an axial sectional view of a mouthpiece for a breath alcohol measuring device constructed in accordance with the invention.

Referring to the drawings in particular the invention embodied therein in FIG. 1 comprises a one piece mouthpiece for a breath alcohol measuring device which comprises a hollow cylindrical mouth portion 1 having an open tubular mouth engaging end 1a and an opposite partly closed end 1b.

A hollow tubular connecting portion has an open exterior end 2a and an opposite interior closed end having a closed top 6 which terminates at the interior 5 of the mouth portion 1. The mouth portion 1 has a diameter and a wall thickness suitable for taking the mouthpiece into the mouth and it has a radial flange on its exterior at 8 which limits the outside length of penetration of the mouth portion into a person's mouth.

The mouthpiece 20 shown in FIG. 1 is an integral part injection-molded of polypropylene. The part comprises a hollow-cylindrical mouth portion 1, and a connecting portion 2 which is cylindrical and has a diameter fitting the respective connections of the breath alcohol measuring device. Connecting portion 2 concentrically extends through a partly closed bottom 3 of the mouth portion 1 and it has a breath intake end 4 which projects in the interior 5 thereof. This end 4 is closed on its top 6 and it is provided with lateral breath intake apertures 7. With the mouthpiece in use, the mouth portion 1 is held by the tested person between his lips. The radial limiting flange 8 limits the amount of introduction of the mouth portion 1 into the mouth and makes sure that the outside surface 9 remains free from saliva. The mouthpiece 10 can thus be removed in a hygienic way. The particular design of the breath intake end 4 of connecting portion 2 prevents saliva particles from being entrained into the measuring device.

Figure 2:
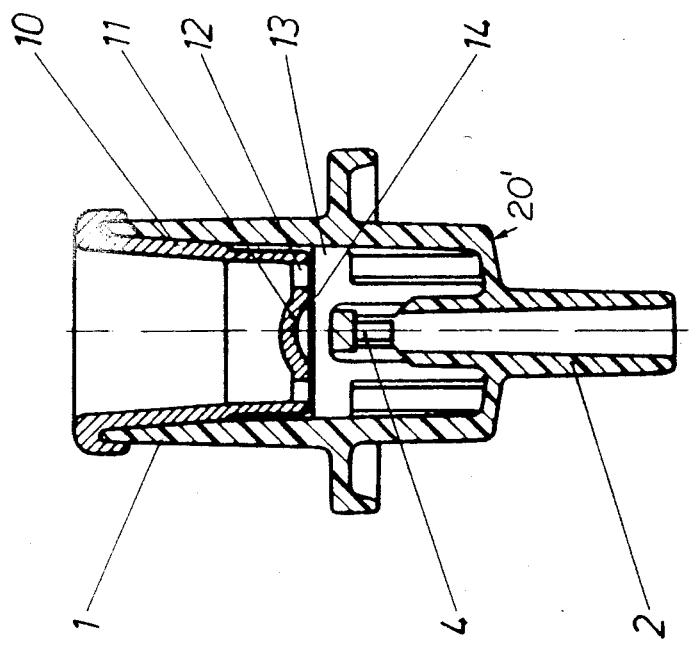
FIG. 2 is a view similar to FIG. 1 of another embodiment of the invention.

In accordance with FIG. 2, a mouthpiece 20' can easily be equipped with a check valve. A valve intake 10 is inserted in a mouth portion 1. The insert 10 is designed with a bottom 11 which is provided with off-center perforations 12 for the exhaled breath air. A valve plate or check valve 14 of an elastic material such as polyethylene or polyvinylchloride is held in position in the space 13 between bottom 11 and breath intake end 4 of connecting portion 2. The check valve opens when breath is blown into the mouthpiece 20'. This causes valve plate 14 to move against the closed top end 6 of connecting portion 2, and flex downwardly to permit the breath to pass around the plate 14, into the lateral intake apertures 7 and through the connection portion 2. Upon inhaling, plate 14 is drawn up against the bottom 11 of insert 10 thereby closing off center perforations 12 to prevent inhaling.

While specific embodiments of the invention have been shown and described in detail to illustrate the application of the principles of the invention, it will be understood that the invention may be embodied without departing from such principles.

What is claimed is:

1. A mouthpiece for a breath-alcohol measuring device, comprising: a hollow cylindrical mouth portion (1) having an open tubular mouth engaging end (1a) and an opposite partly closed end (1b); a central hollow tubular connecting portion (2) having an open outer end (2a) and an opposite inner closed top end (6), said connecting portion closed top end being connected to and extending through said partly closed end (1b) of said mouth portion, into an interior of said mouth portion and having a lateral inlet opening (7) on its side adjacent said inner closed top end, which inlet opening opens into the interior of said mouth portion (1) and communicates the hollow cylindrical mouth portion with the inlet opening of said connecting portion for the flow of breathing gas through said connecting portion from the open outer end thereof; said mouth portion having a diameter and wall thickness suitable for taking the mouth portion into a person's mouth and including an exterior flange (8) projecting radially outwardly from an exterior of said mouth portion at a spaced location from its open end (1a) and being of a size wider than the person's mouth to limit the length of penetration of the mouth portion into the person's mouth up to the flange; said mouth portion, said flange and said connecting portion being made of one piece of plastic material; a tubular insert member (10) engaged into said mouth portion open end and having an inner end portion (11) overlying and spaced from said closed top end (6) of said connecting portion (2) with an off-center opening (12) therethrough; and an elastic valve plate (14) disposed in the space between said inner end portion (11) and said closed top end (6) and being free to move between the closed top end of said connecting portion and said insert member and being bendable against said closed top end (6) during blowing into said mouth portion to permit the breathing gas to flow around said plate and into the lateral inlet opening (7) of said connecting portion and being movable against said inner end portion (11) of said insert member during inhaling to close the off-center opening of said insert member inner end portion.

2. A mouthpiece according to claim 1, wherein said one piece of material comprises an injection molded part, said valve plate being made of polyethylene.

3. A mouthpiece according to claim 1, wherein said one piece of material is an injection molded part and said valve plate is made of polyvinylchloride.

* * * * *